United States Patent [19]

Widin et al.

[11] Patent Number: 4,944,301

[45] Date of Patent: Jul. 31, 1990

[54] METHOD FOR DETERMINING ABSOLUTE CURRENT DENSITY THROUGH AN IMPLANTED ELECTRODE

[75] Inventors: Gregory P. Widin; Christopher van den Honert, both of St. Paul, Minn.

[73] Assignee: Cochlear Corporation, Englewood, Colo.

[21] Appl. No.: 207,774

[22] Filed: Jun. 16, 1988

[51] Int. Cl.⁵ ............................................. A61N 1/36
[52] U.S. Cl. .................................................. 128/420.6
[58] Field of Search ............. 128/420.5, 420.6, 419 P, 128/419 R, 419 PT, 419 C, 784

[56] References Cited

U.S. PATENT DOCUMENTS

| | | | |
|---|---|---|---|
| 2,808,826 | 10/1957 | Reimer et al. | 128/2.1 |
| 3,000,271 | 9/1961 | Harvey et al. | 128/2.1 |
| 3,557,775 | 1/1971 | Mahoney | 128/1 |
| 3,563,231 | 2/1971 | Ducote et al. | 128/2.1 |
| 3,794,017 | 2/1974 | Servos | 128/2.1 |
| 4,023,561 | 5/1977 | Servos | 128/2.1 |
| 4,164,214 | 8/1979 | Stark et al. | 128/741 |
| 4,357,497 | 11/1987 | Hochmair et al. | 179/107 |
| 4,400,590 | 8/1983 | Michelson | 179/107 |
| 4,419,995 | 12/1983 | Hochmair et al. | 128/419 |
| 4,441,210 | 4/1984 | Hochmair et al. | 455/41 |
| 4,499,339 | 2/1985 | Richard | 179/107 |
| 4,592,359 | 6/1986 | Galbraith | 128/419 |
| 4,595,018 | 6/1986 | Rantala | 128/733 |
| 4,617,913 | 10/1986 | Eddington | 128/1 |

OTHER PUBLICATIONS

Desoyer et al, "An Eight Channel Scale . . . ", IEEE Trans. Biomed. Eng., vol. BME-27, No. 1, Jan. 1980, pp. 44-50.
Mercer et al, "Photolithographic Fabrication . . . Stimulation", IEEE Trans. Biomed. Eng., vol. BME-25, No. 6, Nov. 1978, pp. 494-500.
W. G. Wolcomb et al., "A Demand Radiofrequency Cardiac Pacemaker", Med. & Biol. Engng., vol. 7, pp. 493-499.
G. Plicchi et al., "An Implantable Cardiac Pacemaker".
M. Patel et al., "Implanted Pacemaker Evaluation Using Graphic Method on PDP".
P. Mancini et al., "A New Method for Utilizing a Standard Electrocardiograph for In Vivo Clinical Pacemaker Analysis", IEEE Transactions on Biomedical Engineering, vol. BME-22, No. 4, Jul. 1975.
N. Thakor, "From Holter Monitors to Automatic Defibrillators: Developments in Ambulatory Arrhythmia Monitoring", IEEE Transactions on Biomedical Engineering, vol. BME-22, No. 12, Dec. 1984.
D. L. Thomas et al., "A Pacemaker Digital Electrocardiograph for Accurate Assessment of Implanted Cardiac Pacemakers", Med. & Biol. Engng., vol. 9, pp. 503-509.
Brochure by Otologic Products/3M 1986 "Cochlear Implant System—What to Expect with a Cochlear Implant—Questions and Answers".

(List continued on next page.)

Primary Examiner—Lee S. Cohen
Attorney, Agent, or Firm—Gottlieb, Rackman & Reisman

[57] ABSTRACT

A method for determining absolute current density through an implanted electrode measures the fundamental and harmonic components of an electrical current passing through the electrode and estimates the absolute current density from the ratio between the magnitude of the electrical current measured at one of the harmonics on the fundamental frequency. Another method of the invention applies a wideband noise input voltage to the electrode under investigation and measures the spectrum of the input voltage and output current to determine a first transfer function. A second transfer function representing an increase magnitude of wideband noise input voltage is also obtained. A difference transfer function is computed and used to determine absolute current density through the electrode. The methods may be practiced non-invasively.

18 Claims, 2 Drawing Sheets

OTHER PUBLICATIONS

Publication by *Hearing Instruments* "The Cochlear Implant—1985", vol. 35 #6, Jun. 1985.

Brochure by *Otologic Products/3M* 1986, "Most of Us Seek Occasional Moments of Quiet and Solitude, But for Some, All Their Moments Are Quiet".

Cathy Bell et al., "The Egg and Chronic Cerebellar Stimulations: The Utility of Artifact", *Am. J. EEG Technol.*, 19:1–8, 1979.

Betty Longwith, "Implant User Establishes Club for Hearing Impaired"; Brochure by *Otologic Products/3M* 1985.

S. B. Brummer et al., "Electrical Stimulation with PT Electrode Areas", *IEEE Transactions on Biomedical Engineering*, vol. BME-24, No. 5, Sep. 1977.

Gregory P. Widin et al., "Perceptual Similarity of Complex Signals Presented by Electrical Stimulation of the Auditory Nerve", *Journal of the Accoustical Society of America*, 1985, 77 Suppl. 1, SB1.

V. M. Kirby et al., "Loudness of Complex Signals Presented by Electrical Stimulation of the Auditory Nerve", *Journal of the Accoustical Society of America*, 1985, 77 Suppl. 1, SB1.

METHOD FOR DETERMINING ABSOLUTE CURRENT DENSITY THROUGH AN IMPLANTED ELECTRODE

TECHNICAL FIELD OF THE INVENTION

This invention relates to implant systems utilizing implanted electrodes, and in particular to a method for assessing the function of an implanted electrode in such an implant system.

BACKGROUND OF THE INVENTION

Electronic hearing systems utilizing implanted electrodes to electrically stimulate the auditory nerve are increasingly used to produce the sensation of hearing in the deaf. Examples of such systems are disclosed in U.S. Pat. Nos. 4,419,995 and 4,617,913. The quality of the electrode/tissue connection is of primary importance to the performance of any implanted electrode system. In particular, the quality of the connection directly affects the level of current that can be applied through an electrode, and consequently the quality and intensity of the electrical stimulation delivered to the auditory nerve.

The absolute current density of current flowing through an implanted electrode is an important parameter of its function. If the absolute current density through an electrode is too high, unwanted irreversible reactions can occur. For instance, metals and chemicals from the electrode may be released into the surrounding tissue, or in extreme cases body fluids may be hydrolyzed.

Information on absolute current density is thus of considerable value for the purpose of fitting an implant system to be sure that it is operating within safe limits. Absolute current density also can be used to identify an internal shunt which is disrupting the operation of the electrode, or to measure the stability of an implant system over time. Thus, it would be highly desirable if a simple and practical method for determining absolute current density through an implanted electrode were available.

SUMMARY OF THE INVENTION

The present invention provides a method for determining absolute current density through an implanted electrode. According to one method, a periodic voltage is applied across an active electrode under investigation and a ground or indifferent electrode. Next, the current waveform carried through the active electrode is measured at the fundamental frequency of said periodic voltage and at one or more harmonics of the fundamental frequency. Finally, the ratio in magnitude between the current waveform measured at the fundamental frequency and the current waveform measured at one or of said harmonics is used to estimate the absolute current density carried through the active electrode.

According to one important aspect of the invention, the current waveform through the active electrode can be measured from the electrical potential appearing on the skin of the patient. Thus, the method can be performed readily and non-invasively.

According to an alternative method according to the present invention, a wideband noise input voltage is applied across the active electrode under investigation and a ground or indifferent electrode. The spectrum of the input voltage $V_1(jw)$ and output current $I_1(jw)$ are measured. Using these functions, a first transfer function $H_1(jw)$ is determined as a ratio of $I_1(jw)$ to $V_1(jw)$. Next, the wideband noise input voltage is increased and further measurements are taken to establish $V_2(jw)$ and $I_2(jw)$ for the increased magnitude input voltage. A second transfer function $H_2(jw)$ is then computed as the ratio of $I_2(jw)$ to $V_2(jw)$. Finally, the absolute current density is estimated from the difference between $H_2(jw)$ and $H_1(jw)$. According to another aspect of this alternative method, the spectrum of the output current can be measured from the voltage potential appearing on the patient's skin.

Thus, it can be seen that the present invention provides methods for readily and non-invasively obtaining a measure of the absolute current density through an implanted electrode in an implant system.

DETAILED DESCRIPTION OF THE INVENTION

The present invention is of value in assessing the function of implanted electrodes in an implant system utilizing electricity to stimulate body tissue. The present invention is described herein with specific reference to its use in assessing the function of implanted electrodes in an electronic hearing system. It shall be understood, however, that the methods of the invention are in no way limited to use in connection with electronic hearing systems, but rather can be used in connection with any implant system using implanted electrodes. For instance, the present invention would be useful in assessing implanted electrode function in subcutaneous electrical tissue or muscle stimulators.

Figure 1:
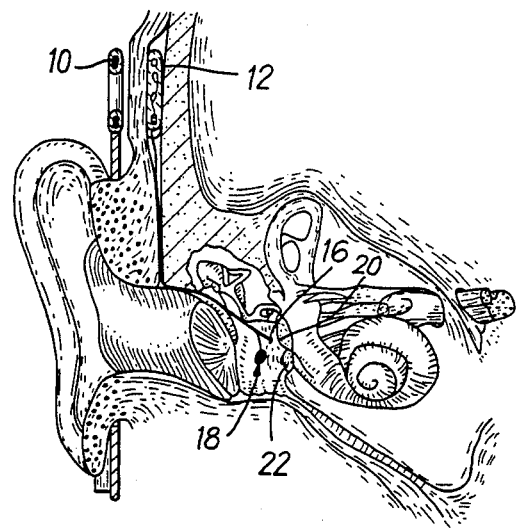
FIG. 1 is a cross-sectional view showing the physiological aspects of the human ear and the positioning of a pair of electrodes in the cochlea; and FIG. 2A, FIG. 2B

A typical disposition of implanted electrodes in the human ear is illustrated in FIG. 1. As shown in FIG. 1, electrode 16 is an active electrode while electrode 18 comprises a ground or indifferent electrode. The active electrode 16 is shown affixed near the base of the cochlea, for instance to the promontory bone 20 or to the round window membrane 22.

Electrodes 16 and 18 are shown as part of a Vienna-type cochlear implant system, for instance as described in U.S. Pat. No. 4,419,995, in which they are connected to the output of an implanted receiver module 12, through an insulated lead 14. Receiver module 12 is positioned to receive an RF signal from an external transmitter coil 10, which is driven by an external unit carried by the patient. As is conventional in a Vienna-type system, the external unit (not shown) converts soundwaves in the patient's environment to electrical signals which are used to activate a transmitter in the unit. The transmitter drives coil 10 to transmit modulated RF to the implanted module 12. Receiver module 12 demodulates the RF signal to produce a stimulation voltage corresponding to the soundwaves picked up by the external unit. The stimulation voltage is applied across the active electrode 16 and the ground or indifferent electrode 18 to generate electrical current through the cochlear tissue, thereby stimulating the auditory nerve. Further information on the operation of such a Vienna-type system can be found in U.S. Pat. No. 4,419,995, the entire disclosure of which is hereby incorporated herein by reference.

By way of example, the active electrode 16 may comprise a small bead or disk formed on the end of the insulated wire lead 14 and may have a diameter of, for example, 1.5–2.0 millimeters. The ground or indifferent electrode 18 is normally positioned within the middle ear, approximately 2–10 millimeters from the active electrode 16. The indifferent electrode 18 is preferably approximately two to three times larger in area than the active electrode 16. The current density at the site of the active electrode is thus several times greater than at the site of the indifferent electrode, insuring that the stimulation is focused at the point of contact of the active electrode 16.

With metal electrodes in an ionic environment, the I-V characteristics of the electrode/tissue connection are non-linear. For example, if a sinusoidal voltage were applied across implanted electrodes 16 and 18 in the system of FIG. 1, and the current waveform through the circuit was measured, the current waveform would not be sinusoidal due to harmonic distortion introduced by the non-linear I-V characteristics of the electrode/tissue connection. These non-linear characteristics result from changes in the complex impedance seen at the electrodes as the result of various electrochemical processes. Changes in complex impedance can be caused, for example, by gassing at the electrode surface and by level dependent changes in electrode-protein interactions.

It has been found that the higher the current density through an implanted electrode, the greater the effects of distortion. Moreover, it has been found that the magnitude of the harmonics of the applied waveform increase with the level of distortion. Thus, absolute current density is related to the magnitude of the harmonics. This relationship is utilized by the methods of the present invention to estimate absolute current density.

An example of the harmonic distortion resulting from the non-linear I-V characteristics of the electrode/tissue connection is illustrated in FIG. 2, which shows graphs of data obtained from an experiment in which an electrode pair similar in construction to the above-described electrodes 16 and 18 were placed in a physiological saline to simulate their operation as implanted. In the experiment, a sinusoidal voltage signal of a known magnitude was applied across the electrodes and the first three harmonics of the fundamental frequency of the signal were measured, for varying absolute current densities.

To determine absolute current density in the active electrode, the surface area of the active electrode was determined and the absolute current density was calculated (the measured known current $J_0$ through the electrode divided by the surface area). The surface area of the active electrode can be determined by microscopic or electrochemical methods such as those described in the article "Electrical Stimulation with Pt Electrodes: 1—A Method for Determination of 'Real' Surface Areas" by Bremmer & Turner, IEEE Trans. Biomed. Eng 24(5): 436–439, 1977.

In graphs A, B and C of FIG. 2, the magnitude of the currents $J_1$, $J_2$, $J_3$ of each of the respective harmonics is referenced to the magnitude of the fundamental in decibels, and is plotted against the absolute current density of $J_0$ in $uA/mm^2$ at the fundamental frequency. As may be seen in each graph, the ratio between the magnitude of the harmonic and fundamental increases as the absolute current density of the current waveform $J_0$ increases. The ratio between the magnitude of a harmonic and the fundamental frequency can thus be used to determine the absolute current density through the electrode under investigation. It is contemplated that even more accurate estimates of absolute current density can be derived by averaging estimates obtained from each of the harmonics.

The harmonic characteristics of an electrode are affected by its composition, i.e. the type of metal used to fabricate the electrode, and by the process by which the electrode is fabricated, e.g. whether it is etched, annealed or sputtered. In addition, the harmonic characteristics of an electrode are also influenced by the fluid environment of the electrode. Thus, to practice the method of the present invention it is preferred to first perform a calibration step in which the harmonic characteristics of the electrode pair to be investigated are established. For example, a calibration procedure would be performed on a particular type of electrode pair to be used in implant procedures. The calibration data obtained can then be used to determine absolute current density for all implants of that particular type of electrode.

Figure 2A:
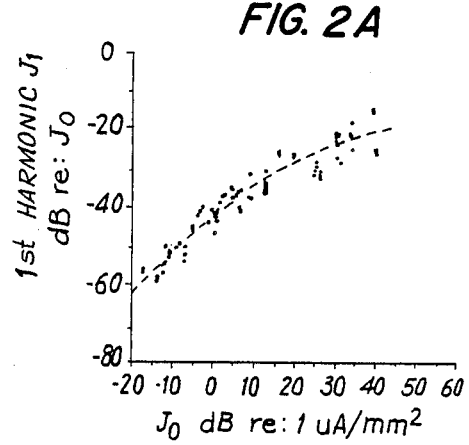
FIG. 2C shows three example graphs of data demonstrating the relationship between absolute current density and harmonics of the fundamental frequency of an applied waveform.
Figure 2B:
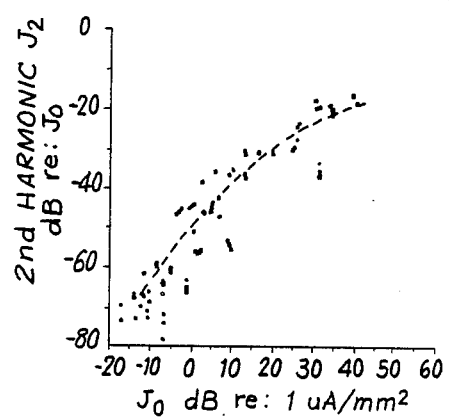
Figure 2C:
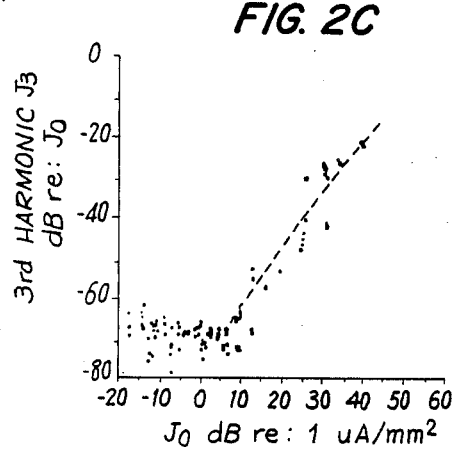

During the calibration procedure, graphs such as those shown in FIG. 2A, FIG. 2B and FIG. 2C are developed for one or more harmonics. The calibration procedure is preferably performed ex-vitro using a physiological saline having a chemical composition as close to the typical make-up of human tissue fluid as possible, for example a proteinated saline. Alternatively, the calibration can be performed in-vivo in animals. In-vivo calibration in human subjects is not practical because determination of high absolute current density performance could be injurious to the patient. In any event, the idea is to calibrate the electrodes pair in an environment as close to that in which it will be implanted, i.e. human tissue in the case of human implant.

Once calibration data has been obtained for an electrode pair, the preferred embodiment of the method of the present invention is carried out as follows:

(1) a periodic voltage signal is applied across the pair of implanted electrodes under investigation, with the voltage signal having a fundamental frequency;
(2) the current waveform through the electrode circuit is measured at the fundamental frequency of the voltage signal;
(3) the current waveform through the electrode circuit at one or more harmonics of the fundamental frequency is measured;
(4) the ratio of the magnitudes of the current waveform measured at one of the harmonics and the fundamental frequency is determined; and
(5) the absolute current density through the active electrode is estimated from reference to the corresponding harmonic calibration data (graph). More specifically, the value of the ratio for the harmonic being used is located on the curve of the corresponding calibration graph for that harmonic, and the corresponding absolute current density is found on the abscissa of the graph. Alternatively, an absolute current density estimate can be derived by averaging several estimates obtained for different harmonics.

Because it is only necessary to know the ratio between a harmonic and the fundamental to estimate absolute current density, a direct measure of the current waveform through the electrodes is not required. Rather, a relative or proportional measure of the current waveform at the fundamental and harmonic can be used so long as both have a common reference. One such relative measure of the current waveform can be obtained by measuring the electrical potential appearing on the skin of the patient. Because the human body tissue is to a good approximation resistive for frequencies up to twenty (20) KHz, current flowing through the body tissue generates a proportional voltage on the skin of the patient. In the case of a cochlear implant system as shown in FIG. 2, this potential can be measured with a high impedance amplifier using, for example, a standard evoked-response electrode configuration. An indirect measure of the currents flowing through the cochlea at the fundamental and harmonics, and thus the electrode system, can thus be obtained. Since these voltage waveforms are in the same relative proportions to one another as the current waveforms themselves, these indirect measures can be used to derive the ratio of the harmonic to the fundamental. This ratio can be used to estimate absolute current density from the calibration data in the same manner as described above using direct measures of the current waveforms.

In addition to the above-described method, the present invention contemplates an alternative method for utilizing the non-linear I-V characteristics of the electrode/tissue interface for determining the absolute current density of current flowing through an implanted electrode. This method is contemplated to be preferred over the above-described method in the case of very low currents which make it difficult to make meaningful enough distortion measurements to obtain reliable estimates.

In this alternative method, the transfer function comprising the ratio of the output current spectrum to the input voltage spectrum is measured for different input voltages. Because the system is non-linear, the transfer function varies with the input magnitude. Accordingly, the absolute current density flowing through an implanted electrode can be estimated from the change in the transfer function from one input voltage level to another. Preferably, a wideband noise input voltage is used for this purpose.

The alternative method of the present invention requires a calibration procedure similar to that specified above for the other embodiment of the invention. This calibration procedure is as follows:

(1) The surface area of the active electrode to be calibrated is measured (by microscopy or electrochemical methods);
(2) A selected wideband voltage signal is applied to the active and indifferent electrode pair and is adjusted in its intensity until the measured RMS (root-mean-square) absolute current density (i.e. RMS current divided by electrode surface area) is at the lowest value for which the method is to be used;
(3) The voltage spectrum $V_N(jw)$ and current spectrum $I_N(jw)$ are measured;
(4) The transfer function $H_N(jw) = I_N(jw)/V_N(jw)$ is computed;
(5) The intensity of the wideband voltage is increased by a small amount (the size of the increase is determined by the desired accuracy);
(6) The absolute current density for the increased voltage is determined;
(7) Steps 3 and 4 are repeated, resulting in a second transfer function $H_{N+1}(jw)$;
(8) A difference spectrum $D_N(jw) = N_{N+1}(jw) - H_N(jw)$ is computed;
(9) Steps 5, 6, 7 and 8 are repeated (always using the same amount of increase in the voltage intensity) until the current density reaches the highest value for which the method is to be used, resulting in many different spectra:

$$D_1(jw) = H_2(jw) - H_1(jw)$$

$$D_2(jw) = H_3(jw) - H_2(jw)$$

$$D_3(jw) = H_4(jw) - H_3(jw)$$

$$D_N(jw) = H_{N+1}(jw) - H_N(jw)$$

These N difference spectra each correspond to a particular absolute current density (determined in step 6) above) and are the calibration spectra to be used to estimate absolute current density using this alternative method. These spectra are preferably plotted for later reference in the estimation step of this alternative method, as more fully described below.

Once calibration values for a particular electrode pair is established, the alternative method of determining absolute current density is preferably performed as follows:

(1) a wideband noise input voltage is applied across the implanted electrode pair under investigation;
(2) the spectrum of the input voltage and the output current are measured to determine $V_1(jw)$ and $I_1(jw)$, respectively;
(3) the transfer function $H_1(jw) = I_1(jw)/V_1(jw)$ is computed;
(4) the magnitude of the input voltage applied in step (1) is increased by a small amount;
(5) the spectrum of the input voltage and the output current are re-measured to determine $V_2(jw)$ and $I_2(jw)$, respectively, for the increased input voltage;
(6) the transfer function $H_2(jw) = I_2(jw)/V_2(jw)$ is computed;
(7) the difference $D(jw) = H_2(jw) - H_1(jw)$ is computed; and
(8) the difference transfer function $D(jw)$ is matched to one or more of the calibration spectra to estimate the absolute current density.

The alternative method, like the first-described method, may be performed using either a direct or indirect measurement of the input voltage and output current. The output current may be measured as described above using the voltage appearing on the surface of the patient's skin. The input voltage may be measured directly from where it is applied at its source, as for example, as might be measurable on the electrode leads or it may be measured indirectly, for instance, as the level of input voltage or tone applied to the speech processor or transmitter of an external unit in the case of a Vienna-type cochlear implant system as referred to with respect to FIG. 1.

Thus, there are described above methods for determining the absolute current density flowing through an active electrode in a cochlear implant system. These methods permit the absolute current density to be determined non-invasively using measurements taken from the surface of the patient's skin. The methods may also be implemented wherein the current flow measurements can be obtained directly, as may be possible during the implantation procedure, or as may be possible by including such measurement circuits in an implanted system, with the current measurements being telemetered from the implanted unit to an external device.

This measurement of absolute current density thus provides a measure of the quality and characteristics of the electrode/tissue connection for an implanted electrode. As mentioned above, information on this connection provides valuable feedback on the nature of the connection and on the type of electrode performance that can be expected.

Although the invention has been described herein in its preferred form, those skilled in the art will readily appreciate that many modifications and changes may be made thereto without departing from the spirit and scope of the claims appended hereto.

What is claimed is:

1. A method for determining the absolute density of an electrical current passing through an electrode implanted in a body, comprising the steps of:
    (a) applying a voltage waveform to said implanted electrode;
    (b) measuring the distortion of said waveform introduced by the non-linear I-V characteristics of the interface between said electrode and the tissue of said body; and
    (c) estimating the absolute current density of said electrical current through said electrode based on the characteristics of said distortion.

2. A method according to claim 1 wherein there is provided predetermined calibration data describing the absolute current density through said implanted electrode as a function of the distortion of said waveform, and further wherein said estimated absolute current density is obtained by referencing said data.

3. A method according to claim 1 wherein said distortion measurement of step (b) comprises the steps of:
    (i) measuring the magnitude of current through said electrode at a first frequency in said waveform;
    (ii) measuring the magnitude of current through said electrode at a harmonic of said first frequency; and
    (iii) calculating the ratio of said current measured at said harmonic frequency to said current measured at said first frequency to provide a measure of said distortion.

4. A method according to claim 3 wherein more than one harmonic is measured and wherein the absolute current density is estimated from each of said more than one harmonics, and wherein the estimates obtained for each of said more than one harmonics are averaged together to determine a measure of said distortion.

5. A method according to claim 3, wherein said electrical current measured in steps (i) and (ii) is measured indirectly form the electrical potential appearing on the surface of the body.

6. A method according to claim 1 further wherein in said step (a) the applied waveform voltage comprises a wideband noise and further wherein said step (b) of measuring distortion includes the steps of:
    (i) measuring the frequency spectrum of the input voltage and the current through said electrode to determine $V_1(jw)$ and $I_1(jw)$ respectively;
    (ii) computing the transfer function $$H_1(jw) = \frac{I_1(jw)}{V_1(jw)};$$

(iii) increasing the magnitude of the voltage applied in step (a);
   (iv) measuring the frequency spectrum of the applied voltage and the current through said electrode to determine $V_2(jw)$ and $I_2(jw)$ respectively;
   (v) computing the transfer function $$H_2(jw) = \frac{I_2(jw)}{V_2(jw)}$$

for the increased magnitude voltage;
   (vi) computing the difference between the transfer functions to yield the transfer function $D(jw) = H_2(jw) - H_1(jw)$ as a measure of said distortion.

7. A method according to claim 6 wherein the absolute current density estimated in step (c) is estimated by matching said transfer function $D(jw)$ to one or more of a plurality of N predetermined calibration spectra $D_N(jw)$ each corresponding to an absolute current density.

8. A method according to claim 6 wherein in said step (i) and step (iii) the current frequency spectrum is measured from the electrical potential appearing on the skin of the body.

9. A method for determining the absolute density of an electrical current passing through an electrode implanted in a body, comprising the steps of:
    (a) applying a voltage having a periodic waveform with a fundamental frequency to said implanted electrode;
    (b) measuring the electrical current passing through said implanted electrode at said fundamental frequency;
    (c) measuring the electrical current passing through said implanted electrode at at least one harmonic of said fundamental frequency; and
    (d) estimating the absolute current density from the ratio in magnitude between the value of said electrical current measured at said at least one harmonic of said fundamental frequency and the value of said electrical current measured at said fundamental frequency.

10. A method according to claim 9 wherein there is provided predetermined calibration data describing the absolute current density through said implanted electrode as a function of the ratio of said at least one harmonic to said fundamental frequency, and further wherein said estimated absolute current density is obtained by referencing said data using said ratio.

11. A method according to claim 9 wherein said periodic voltage is sinusoidal.

12. A method according to claim 9 wherein more than one harmonic is measured and wherein the absolute current density is estimated from each of said more than one harmonics, and wherein the estimates obtained for each of said more than one harmonics are averaged together to estimate absolute current density.

13. A method according to claim 12 wherein said calibration data are obtained for said implanted electrode for one of said harmonics according to the following steps:

(a) measuring the surface area of said implanted electrode;

(b) placing said electrode in an environment simulating human physiology;

(c) applying a voltage signal of a known magnitude and fundamental frequency to said electrode;

(d) measuring the current through said electrode at said fundamental frequency;

(e) calculating the absolute current density through said electrode from said measured current and said surface area;

(f) measuring the magnitude of current through said electrode at said harmonic frequency;

(g) calculating the ratio of said current measured at said harmonic to said current measured at said fundamental frequency; and (h) repeating steps (c) through (g) for voltage signals of varying magnitudes to obtain absolute current density measurements corresponding to a range of harmonic to fundamental ratios to provide said predetermined calibration data.

14. A method according to claim 9 wherein said electrical current measured in step (b) and step (c) is measured indirectly from the electrical potential appearing on the surface of the body.

15. A method for determining the absolute current density of an electrical current passing through an electrode implanted in a body, comprising the steps of:

(a) applying a wideband noise input voltage to the electrode;

(b) measuring the spectrum of the input voltage and the output current to determine $V_1(jw)$ and $I_1(jw)$ respectively;

(c) computing the transfer function $$H_1(jw) = \frac{I_1(jw)}{V_1(jw)} ;$$

(d) increasing the magnitude of the input voltage applied in step (a);

(e) measuring the spectrum of the input voltage and the output current to determine $V_2(jw)$ and $I_2(jw)$ respectively;

(f) computing the transfer function $$H_2(jw) = \frac{I_2(jw)}{V_2(jw)}$$

for the increased magnitude input voltage;

(g) computing the difference between the transfer functions to yield $D(jw) = H_2(jw) - H_1(jw)$; and (h) estimating the absolute current density from the difference transfer function $D(jw)$.

16. A method according to claim 15 wherein the absolute current density estimated in step (h) is estimated by matching said transfer function $D(jw)$ to one or more of a plurality N of predetermined calibration spectra $D_N(jw)$ each corresponding to an absolute current density.

17. A method according to claim 16 wherein said calibration spectra are obtained for said electrode according to the following steps:

(a) measuring the surface area of said electrode;

(b) applying a wideband voltage signal to said electrode;

(c) measuring the RMS current through said electrode and computing the RMS absolute current density as the RMS current divided by said surfaces area;

(d) measuring the voltage spectrum $V_N(jw)$ and current spectrum $I_N(jw)$ of the signal carried through said electrode;

(e) computing the transfer function $H_N(jw) = I_N(jw)/V_N(jw)$;

(f) increasing said wideband voltage signal by a small amount;

(g) determining the absolute current density for the increased voltage signal;

(h) repeating steps (d) and (e) to yield the transfer function $$H_{N+1}(jw) = \frac{I_{N+1}(jw)}{V_{N+1}(jw)} ;$$

(i) computing the difference spectrum $D_N(jw) = H_{N+1}(jw) - H_N(jw)$;

(j) repeating steps (f), (g), (h) and (i) to obtain the difference spectra $D_1(jw), D_2(jw), D_3(jw) \ldots D_N(jw)$, with each spectra corresponding to a particular absolute current density through said electrode.

18. A method according to claim 15 wherein in said step (b) said output current spectrum is measured from the electrical potential appearing on the skin of the body.

* * * * *